United States Patent
Chiou et al.

(10) Patent No.: US 10,945,929 B2
(45) Date of Patent: Mar. 16, 2021

(54) ANHYDROUS COMPOSITIONS AND ARTICLES FOR MAKEUP REMOVAL

(71) Applicant: L'OREAL, Paris (FR)

(72) Inventors: Catherine Chiou, Saddle Brook, NJ (US); Ryuji Hara, Westfield, NJ (US); Michael Robinson, Brooklyn, NY (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/532,018

(22) Filed: Aug. 5, 2019

(65) Prior Publication Data

US 2021/0038484 A1    Feb. 11, 2021

(51) Int. Cl.
| | |
|---|---|
| A61K 8/00 | (2006.01) |
| A61K 8/02 | (2006.01) |
| A61K 8/31 | (2006.01) |
| A61K 8/33 | (2006.01) |
| A61K 8/34 | (2006.01) |
| A61K 8/37 | (2006.01) |
| A61K 8/49 | (2006.01) |
| A61K 8/85 | (2006.01) |
| A61K 8/86 | (2006.01) |
| A61Q 1/14 | (2006.01) |

(52) U.S. Cl.
CPC ............ *A61K 8/0208* (2013.01); *A61K 8/31* (2013.01); *A61K 8/33* (2013.01); *A61K 8/34* (2013.01); *A61K 8/37* (2013.01); *A61K 8/498* (2013.01); *A61K 8/85* (2013.01); *A61K 8/86* (2013.01); *A61Q 1/14* (2013.01); *A61K 2800/596* (2013.01)

(58) Field of Classification Search
CPC ........ A61Q 19/00; A61Q 1/14; A61Q 19/005; A61Q 19/007
See application file for complete search history.

(56) References Cited

U.S. PATENT DOCUMENTS

| | | | |
|---|---|---|---|
| 6,202,845 B1* | 3/2001 | Hill ...................... | A47K 10/421 206/209 |
| 2004/0180020 A1* | 9/2004 | Manelski ............... | A61Q 19/00 424/70.12 |
| 2011/0033509 A1* | 2/2011 | Simon .................... | A61Q 19/00 424/401 |
| 2015/0034116 A1 | 2/2015 | Salese et al. | |

(Continued)

FOREIGN PATENT DOCUMENTS

| | | |
|---|---|---|
| EP | 2986767 B1 | 3/2019 |
| FR | 2897262 A1 | 8/2007 |

OTHER PUBLICATIONS

PCT Notification of Transmittal of the International Search Report and the Written Opinion of the International Searching Authority, or the Declaration, issued to PCT/US2020/044916 dated Nov. 2, 2020.

(Continued)

*Primary Examiner* — John R Hardee
(74) *Attorney, Agent, or Firm* — McNees Wallace & Nurick LLC (57) ABSTRACT

Makeup removal compositions include at least one branched, alkylated alcohol ester; one or a combination of dialkylated ether and dialkylated carbonate; at least one nonionic surfactant; and at least one vegetable derived oil, wherein the composition is essentially free of water. Articles include the composition infused in a water-insoluble or water-soluble substrate.

20 Claims, 4 Drawing Sheets

(56) References Cited

U.S. PATENT DOCUMENTS

| | | | |
|---|---|---|---|
| 2016/0120778 A1* | 5/2016 | Greco | A47K 7/02 |
| | | | 514/512 |
| 2017/0172904 A1 | 6/2017 | Page et al. | |
| 2018/0163325 A1 | 6/2018 | Glenn, Jr. et al. | |
| 2018/0296460 A1 | 10/2018 | Wong et al. | |

OTHER PUBLICATIONS

Mintel, "High Performance Cleansing Oil", XP055742058, Sep. 17, 2008, http://www.gnpd.com.
Mintel, "Anti/Oxi Skin Refining Anti-Dullness Cleansing Oil", XP055742063, Aug. 1, 2013, http://www.gnpd.com.
Mintel, "Anti-Shine Fresh Cleansing Oil", XP055670637, Mar. 21, 2014, http://www.gnpd.com.
Mintel, "Anti-Shine Fresh Cleansing Oil", XP055742075, May 8, 2014, http://www.gnpd.com.
Mintel, "Sublime Beauty Cleansing Oil", XP055742076, Feb. 24, 2017, http://www.gnpd.com.
Mintel, "Sublime Beauty Cleansing Oil", XP055742081, Oct. 24, 2017, http://www.gnpd.com.
Mintel, "Phantom Cleansing Silks", XP055742088, Jul. 2, 2019, http://www.gnpd.com.
Mintel, "Water Splash Cooling Sun Cushion SPF 50+PA++++", XP055742093, Jun. 5, 2019, http://www.gnpd.com.

\* cited by examiner

ANHYDROUS COMPOSITIONS AND ARTICLES FOR MAKEUP REMOVAL

FIELD

This invention relates to makeup removal and cleansing juice compositions impregnated onto an article, having at least one water-insoluble substrate, or one water-soluble substrate, particularly a wipe.

BACKGROUND

Removal of stubborn makeup has always been a challenge and a consumer pain point, particularly for waterproof mascara, long-wear foundation and longer-lasting lip products. Typical makeup removal products are ineffective in removing stubborn makeup, thus requiring repeated tugging and rubbing on the skin and/or the delicate eye areas, causing irritation. Some oil-based makeup removing products may provide ease of makeup removal but leave behind an unpleasant and greasy skin feel. Accordingly, there is a need for compositions and cleansing wipe articles that will provide easy and efficacious makeup removal in addition to a clean and pleasant skin feel after the use.

SUMMARY

The disclosure provides, in various embodiments, a makeup removal composition, comprising:
  i. at least one branched, alkylated alcohol ester;
  ii. at least one dialkylated ether or dialkylated carbonate;
  iii. at least one nonionic surfactant; and
  iv. at least one vegetable derived oil
  wherein the composition is essentially free of water.

In accordance with the various embodiments, a composition according to the disclosure includes at least each of: a one branched, alkylated alcohol ester; one or a combination of dialkylated ether and dialkylated carbonate; a nonionic surfactant; and a vegetable derived oil, wherein the composition is essentially free of water. In various embodiments, the compositions may include more than one of each of the components, and may further include one or more additives including preservatives, actives, emollients and fragrances In accordance with some embodiments:
  i. each of the at least one branched, alkylated alcohol esters is present from about 10% to about 70% by weight of the composition;
  ii. each of the at least one dialkylated ether, dialkylated carbonate, and combinations thereof is present from about 1% to about 10% by weight of the composition;
  iii. each of the at least one nonionic surfactant is present from about 0.5% to about 5% by weight of the composition; and
  iv. each of the at least one vegetable derived oil is present from about 20% to about 60% by weight of the composition.

In accordance with some embodiments:
  i. the total amount of branched, alkylated alcohol esters is present from about 40% to about 70% by weight of the composition;
  ii. the total amount of dialkylated ether, dialkylated carbonate, and combinations thereof is present from about 2% to about 20% by weight of the composition;
  iii. the total amount of nonionic surfactant is present from about 0.5% to about 5% by weight of the composition; and
  iv. the total amount of vegetable derived oil is present from about 20% to about 60% by weight of the composition In accordance with some embodiments:
  i. the at least one branched, alkylated alcohol ester comprises one or more of isopropyl myristate, isopropyl palmitate, ethylhexyl palmitate;
  ii. the at least one dialkylated ether or dialkylated carbonate comprises one or more of dicaprylyl ether and dicaprylyl carbonate;
  iii. the at least one nonionic surfactant comprises one or more of polyglyceryl-6 dicaprate, polyglyceryl-2 oleate and polyglyceryl-10 dioleate; and
  iv. the at least one vegetable derived oil comprises one or more of *Zea mays* (corn) oil or *brassica campestris* (rapeseed) seed oil.

In some embodiments, the composition comprises at least one preservative. In some embodiments, the at least one preservative is present up to about 1 by weight of the composition. In some embodiments, the preservative comprises phenoxyethanol.

In some embodiments, the composition is essentially free of one or more of silicones and mineral oil.

In some embodiments, a makeup removal and cleansing article is provided comprising:
  a. A substrate comprising a cosmetic wipe;
  b. Impregnated in the substrate a cleansing composition comprising;
    i. at least one branched, alkylated alcohol ester;
    ii. at least one dialkylated ether or dialkylated carbonate;
    iii. at least one nonionic surfactant; and
    iv. at least one vegetable derived oil
      wherein the composition is essentially free of water, and
      wherein the cleansing composition is impregnated onto the substrate in a soaking rate of 250% to 400% by weight of the cleansing composition to the weight of the substrate.

In accordance with the various embodiments, the makeup removal and cleansing article is formed from synthetic materials or formed from natural biodegradable and sustainably sourced natural originated fiber, natural fiber, or regenerated or recycled natural fiber. In some embodiments, the cleansing article is formed of a water insoluble substrate. In some embodiments, the cleansing article is formed of a water soluble substrate. In some particular embodiments the article includes a combination of water-soluble and water-insoluble substrates.

In some particular embodiments, the makeup removal and cleansing article comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these.

In some particular embodiments, the makeup removal and cleansing article comprises one or more non-woven sheets comprising water-soluble fibers, wherein the sheets are soluble in running or standing water having a temperature of 30° C. or less and durable when contacted with an anhydrous formulation comprising 5 wt % of water or less.

In some particular embodiments, the makeup removal and cleansing article comprises water-soluble fibers that comprise polyvinyl alcohols, hydroxy(C1-C6)alkyl celluloses, methylcelluloses, carboxymethylcelluloses, polyvinylpyrrolidones, polyalkylene oxides, gelatins, copolymers of acrylic acid and methacrylic acid, or combinations thereof.

These and other aspects of the invention are set out in the appended claims, and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

BRIEF DESCRIPTION OF THE DRAWINGS

Features and advantages of the general inventive concepts will become apparent from the following detailed description made with reference to the accompanying drawings.

DETAILED DESCRIPTION

The term "article" is understood here to mean the combination composed of a water-insoluble support and a composition impregnated on the support. This article can in particular be a wipe but it can also have any form including those described below. The water-insoluble substrate is absorbent and sufficiently strong not to disintegrate during the use thereof. The use of the article as defined above for caring for the skin or hair and/or cleaning and/or removing makeup from and/or scrubbing the skin.

In some embodiments, the article may be formed of synthetic materials, such as PET (Polyethylene terephthalate, or polyester) and PP (polypropylene), which may be used alone or in combination with natural-based material. And in some embodiments, the article may be formed of sustainable and biodegradable substrates from sources such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton.

Many conventional cosmetic articles, such as wipes, are formed of fossil-based polymeric materials, such as PET (Polyethylene terephthalate, or polyester) and PP (polypropylene), which may be used alone or in combination with natural-based material. Such synthetic substrates are desirable because they are relatively less costly to produce and deliver good tensile strength, however, because they essentially never degrade, they contribute adversely to the environment. With increasing focus in the cosmetics industry on sustainability, there is a need for cosmetic articles that employ solid substrates to draw from sources such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton.

In some embodiments, an article herein is formed of substrates that are obtained from sustainable sources and are biodegradable. In some particular embodiments, these materials are selected from natural originated fiber formed into nonwovens, using fibers such as pulp, viscose, lyocell, cellulose acetate, and cotton. And in certain embodiments, the substrates used to form cosmetic articles are nonwovens of lyocell. According to those embodiments that include natural biodegradable and sustainably sourced fibers, a clear benefit realized is the opportunity to reduce the environmental burden. Other benefits may also be achieved using sustainable and biodegradable substrates. As further described herein, exemplified articles that employ sustainable and biodegradable substrates, particularly lyocell nonwovens, demonstrate unexpected mechanical, textural, and absorbent properties and significantly enhanced performance as compared with competitive cosmetic articles that employ synthetic materials. Also as described herein, exemplified articles that employ sustainable and biodegradable substrates, particularly lyocell nonwovens, demonstrate enhanced performance even as compared with inventive compositions hereof that are imbued in a synthetic substrate.

An article according to the disclosure is moist to the touch. It exhibits the advantage of being comfortable during application to the skin and having a nourishing effect due to the presence of an oily phase. When it is used for cleaning or removing makeup from the skin, an article according to the disclosure is passed over the skin, while possibly leaving it applied for a time sufficient for the makeup products to be dissolved in the impregnating composition of the article, and then the skin is wiped. The skin can also optionally be rinsed subsequently. The article according to the invention is a cosmetic article appropriate for caring for and/or treating the skin of the face, body or hands and for cleaning or removing makeup from the skin of the face and/or body. It can also be used for caring for the hair and for removing makeup from the eyes.

An article according to the disclosure can have any form appropriate to the desired objective. It can constitute a wipe that has a generally rectangular, square or other shape that may be single ply, multiple ply, and may be folded or un-folded. The article can also be in the form of a glove, of a mitten or in any other form appropriate for practical use on the face or the body, for example in the form of a face with holes for the sites of the eyes, nose and/or mouth, or in the form of a makeup-removing fingerstall for application in removing makeup from the eyelashes, or in the form of a single- or double-sided disc which can in particular comprise two sides impregnated with different compositions. The article can also comprise a rough surface which makes possible the exfoliation (scrubbing) of the skin.

In some embodiments, an article herein includes and is formed of a substrate that is soluble, in particular water soluble, or substantially water soluble, as further described herein. In various embodiments, an article may include one or more sheets formed of water-soluble fibers. In some embodiments, the article may include both water insoluble and water-soluble layers. An article layer formed with a water-soluble substrate can be dissolved in the palm of the consumer's hand and can provide a complete, convenient "bottle-free" and essentially waste free cleansing opportunity. In various embodiments, articles may include functionalities that include makeup and dirt removal, exfoliation of skin cells, and skin cleansing.

The terms "anhydrous" and "water free" as used herein in the context of one or more of compositions hereof and substrates for articles, means containing water in an amount that less than 5%, such as less than 3%, such as less than 1% by weight, based on the total weight of the composition or substrate.

"Cosmetically acceptable" means a carrier that is compatible with any keratinous substrate.

"Keratinous substrate" and "keratinous tissue" each includes but is not limited to skin, hair, and nails.

As used herein, the terms "natural originated fiber" refers to fiber materials that are formed by chemical processing that render derivatives based on natural fibers; "natural fiber" means non-derivative forms of natural fibers, and "regenerated/recycled" means natural fibers that are reclaimed from goods formed with such fibers.

The terms "silicone-free" and "mineral oil free" as used herein each means containing less than 5%, such as less than 3%, such as less than 1% by weight, based on the total active weight of the composition, of silicones, such as silicone polymers, for example selected from dimethicone and other silicone oils, and silicon elastomers, and of mineral oil.

As used herein, the term "water-soluble" is used to describe a material or an object that substantially or completely dissolves when exposed to water, in particular at temperatures as described herein. The term "substantially water-soluble," used in reference to water-soluble substrates as may be used herein, reflects the possibility that the substrate may include content in a nominal amount of less than 10% that does not completely dissolve, wherein the insoluble amount is not by design. The terms "water-insoluble" and "insoluble" as used herein in reference to a substrate for forming an article are used to describe a material or an object that substantially or completely is not soluble and does not dissolve when exposed to water and/or an anhydrous composition according to the instant disclosure.

The terms "wipe" and "pad" in reference to articles according to the disclosure are used interchangeably; likewise, the terms "sheet" and "layer" are used interchangeably throughout the disclosure. The wipes disclosed herein are in some embodiments in the form of one or more sheets of fibers. As used herein, a non-woven sheet is a sheet which is different from a thin film.

According to the disclosure, the inventive compositions overcome the shortcomings of the prior art and provide unexpected benefits that include ease with overall makeup removal and easy foundation removal and easy mascara removal (regular and waterproof) with no rubbing, with overall improved efficacy as compared with commercial comparative compositions, including those that include one or more of silicones and mineral oils; leaves skin feeling clean and fresh, soft and smooth; satisfying size and thickness of substrate (wipe); not too dry; non-greasy; does not leave a residue; pleasant fragrance; includes desirable natural based fibers; and can include part or all water soluble fiber substrate.

Through expert evaluations of makeup removal efficacy, compositions and wipes according to the disclosure demonstrated significantly better performance in removing waterproof mascara and long-wear foundation as compared with currently marketed makeup removal wipes, including, for example Neutrogena™ Makeup Remover Cleansing Towelettes and Garnier™ SkinActive Clean+ Refreshing Remover Cleansing Towelettes, both formed with synthetic fiber substrates imbued with cleansing compositions, and the oil based wipes, Shiseido—Clé de Peau Beauté Eye and Lip Makeup Remover Towelettes. The inventive compositions according to the disclosure not only performed better in makeup removal efficacy, including improved performance in the removal of both foundation and mascara, they also provided an experience that was more pleasing and resulted in comparatively better skin feel after use, particularly in comparison with the oil based comparative which includes silicone and mineral oil. Inventive articles formed using natural fiber and water-soluble fiber demonstrated similar enhanced performance versus comparative compositions. The compositions according to the disclosure have a clean feel when applied, and do not leave skin feeling greasy or sticky.

Compositions according to the disclosure include at least each of: a one branched, alkylated alcohol ester; one or a combination of dialkylated ether and dialkylated carbonate; a nonionic surfactant; and a vegetable derived oil. The compositions are free or essentially free of water. In various embodiments, the compositions may include more than one of each of the components, and may further include one or more additives including preservatives, actives, emollients and fragrances.

(i) Branched, Alkylated Alcohol Ester

In accordance with the disclosure, the compositions include at least one branched, alkylated alcohol ester.

In some embodiments, suitable branched, alkylated alcohol esters that may be used according to the disclosure may be chosen from isopropyl myristate, isopropyl palmitate, ethylhexyl palmitate, methyl palmitate, 2-ethylhexyl palmitate, hexyl laurate, ethylhexyl laurate, isopropyl laurate, ethylhexyl oleate, ethylhexyl isononanoate, isononyl isononanoate, myristyl myristate, 2-ethylhexyl caprate/caprylate (or octyl caprate/caprylate), isostearyl neopentanoate, cetearyl ethylhexanoate, isopropyl isostearate, diisopropyl sebacate, coco caprylate/caprate, diisopropyl adipate, and combinations thereof esters of lactic acid and of fatty alcohols comprising 12 or 13 carbon atoms, and combinations thereof.

In some particular embodiments the at least one branched, alkylated alcohol ester includes isopropyl myristate. In some embodiments the composition comprises two or more branched, alkylated alcohol esters. In some such embodiments, the at least one branched, alkylated alcohol ester comprises isopropyl myristate and one or more additional branched, alkylated alcohol ester. In some particular embodiments, the composition comprises isopropyl myristate, isopropyl palmitate, and ethylhexyl palmitate.

In accordance with the various embodiments, each of the at least one branched, alkylated alcohol esters is present from about 10% to about 70% by weight of the composition, or from about 10% to about 60% by weight, or from about 10% to about 40%, or from about 10% to about 30%, or from about 12% to about 25%, or from 18% to about 20% or any suitable combination, sub-combination, range, or sub-range thereof by weight, based on the weight of the composition. The total amount of branched, alkylated alcohol ester present in the composition is in an range of from about 40% to about 70% by weight, or from about 50% to about 65% by weight, or from about 55% to about 58% or any suitable combination, sub-combination, range, or sub-range thereof by weight, based on the weight of the composition. One of ordinary skill in the art, however, will appreciate that other ranges are within the scope of the invention.

Thus, each of the at least one branched, alkylated alcohol ester in the composition may be present by weight, based on the total weight of the composition, from about 10, 15, 20, 25, 30, 35, 40, 45, 50, 55, 60, 65 to about 70 percent, including increments and ranges therein and there between.

(ii) Dialkylated Ether, Dialkylated Carbonate

In accordance with the various embodiments, the compositions include at least one dialkylated ether and/or dialkylated carbonate. In some embodiments, the at least one dialkylated ether and/or dialkylated carbonate may be selected from dicaprylyl ether, dicaprylyl carbonate, distearyl ether, hydroxystearyl behenyl ether, hydroxystearyl alkyl C18/C22 ether, diisononyl ether, PPG-11 stearyl ether, isosorbide octyl ether, methyl perfluoroisobutyl ether, ethyl perfluoroisobutyl ether, propylene carbonate, diethylbutyl carbonate, diisoamyl carbonate, and combinations thereof.

In some embodiments the composition comprises one dialkylated ether and/or dialkylated carbonate. In some embodiments the composition comprises at least dialkylated ether and at least one dialkylated carbonate. In some embodiments, the at least one of dicaprylyl ether and dicaprylyl carbonate and one or more additional dialkylated ether and/or dialkylated carbonate. In some particular embodiments, the composition comprises dicaprylyl ether and dicaprylyl carbonate.

In some embodiments, each of the at least one dialkylated ether and/or dialkylated carbonate in the composition is present from about 1% to about 10%, or from about 1% to about 5%, or from about 2% to about 3%, or from about 2% to about 4%, or from about 3% to about 5%, or any suitable combination, sub-combination, range, or sub-range thereof by weight, based on the weight of the composition. One of ordinary skill in the art, however, will appreciate that other ranges are within the scope of the invention.

In some particular embodiments, the total amount of dialkylated ether and/or dialkylated carbonate is present from about 2% to about 20%, or from about 2% to about 10%, or from about 2% to about 4%, or from about 3% to about 5%. In some embodiments the total amount of alkylated glycerol ester/surfactant does not exceed about 2%. In some particular embodiments, the total amount of alkylated glycerol ester/surfactant is less than about 2%.

Thus, each of the at least one dialkylated ether and/or dialkylated carbonate is present by weight, based on the total weight of the composition, from about 1, 2, 3, 4, to about 5 percent, including increments and ranges therein and there between.

(iii) Nonionic Surfactant

In accordance with the various embodiments, the compositions include at least one nonionic surfactant. In some embodiments, the at least one nonionic surfactant may be selected from polyglyceryl nonionic surfactants are selected from the group consisting of polyglyceryl esters, polyglyceryl ethers, polyglyceryl sorbitan fatty acid esters, combinations of two or more thereof and the like. In some embodiments, the at least one nonionic surfactant is selected from polyglyceryl esters, polyglyceryl ethers, and combinations of two or more thereof. In some embodiments, the at least one nonionic surfactant is selected from polyglyceryl-2 oleate, polyglyceryl-4 caprylate/caprate, polyglyceryl-5 caprylate/caprate, polyglyceryl-6 dicaprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-11 oleate, polyglyceryl-12 oleate, polyglyceryl-10 stearate, polyglyceryl-11 stearate, polyglyceryl-12 stearate, and combinations of two or more thereof.

In some embodiments the composition comprises one nonionic surfactant. In some embodiments the composition comprises at least two or more nonionic surfactants. In some embodiments, the composition comprises, polyglyceryl-6 dicaprate polyglyceryl-2 oleate, and polyglyceryl-10 dioleate.

In some embodiments, each of the at least one nonionic surfactant in the composition is present from about 0.5% to about 5%, or from about 0.5% to about 3%, or from about 1% to about 3%, or from about 2% to about 4%, or from about 1% to about 2%, or any suitable combination, sub-combination, range, or sub-range thereof by weight, based on the weight of the composition. One of ordinary skill in the art, however, will appreciate that other ranges are within the scope of the invention.

In some particular embodiments, the total amount of nonionic surfactant is present from about 0.5% to about 5%, or from about 2% to about 4%, or from about 2% to about 3%, or from about 3% to about 5%, or any suitable combination, sub-combination, range, or sub-range thereof by weight, based on the weight of the composition. One of ordinary skill in the art, however, will appreciate that other ranges are within the scope of the invention.

Thus, each of the at least one dialkylated ether and/or nonionic surfactant is present by weight, based on the total weight of the composition, from about 0.5, 1, 2, 3, 4, to about 5 percent, including increments and ranges therein and there between.

(iv) Vegetable Derived Oil

In accordance with the various embodiments, the compositions include at least one vegetable derived oil. In some embodiments, the at least one vegetable derived oil may be selected from *Zea mays* (corn) oil, *brassica campestris* (rapeseed) seed oil, *butyrospermum parkii* (shea) butter, *prunus* amygdalus *dulcis* (sweet almond) oil, *prunus armeniaca* (apricot) kernel oil, and *Helianthus annuus* (sunflower) seed oil, calophyllum, palm, *Ricinus communis* (castor), *Elaeis guineensis* (palm), avocado oil, *Simmondsia chinensis* (jojoba) seed oil, *Olea europaea* (olive) oil, *Cocos nucifera* (coconut) oil, and cereal germ oil, caprylic/capric triglyceride, *Sesamum indicum* (sesame) seed oil, *Triticum vulgare* (wheat) germ oil, argania spinose kernel oil, *Glycine soja* (soybean) oil, canola oil, *Oryza sativa* (rice) bran oil, and combinations thereof.

In some embodiments the composition comprises one vegetable derived oil. In some embodiments the composition comprises at least two vegetable derived oils. In some embodiments, the at least one vegetable derived oil is one of *Zea mays* oil and rapeseed oil. In some particular embodiments, the composition comprises *Zea mays* oil and rapeseed oil.

In accordance with the various embodiments, each of the at least one vegetable derived oil is present from about 20% to about 60% by weight of the composition, or from about 25% to about 55% by weight, or from about 30% to about 45%, or from about 35% to about 40%, or from about 20% to about 25%, or any suitable combination, sub-combination, range, or sub-range thereof by weight, based on the weight of the composition.

The total amount of vegetable derived oil present in the composition is in an range of from about 20% to about 60% by weight, or from about 20% to about 40% by weight, or from about 20% to about 25%, or from about 35% to about 40% by weight or any suitable combination, sub-combination, range, or sub-range thereof by weight, based on the weight of the composition. One of ordinary skill in the art, however, will appreciate that other ranges are within the scope of the invention.

Thus, each of the at least one vegetable derived oil in the composition may be present by weight, based on the total weight of the composition, from about 20, 25, 30, 35, 40, 45, 50, 55, to about 60 percent, including increments and ranges therein and there between.

Solvents

In accordance with the disclosure, the compositions may include one or more solvents. In some embodiments, the solvent is a branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some particular embodiments, suitable liquid alkanes that may be used according to the disclosure include hydrocarbon-based oils containing from 8 to 16 carbon atoms, and especially branched C8-C16 alkanes such as C8-C16 isoalkanes. In some particular embodiments, such liquid alkanes may be chosen from isoparaffins, for instance isododecane (also known as 2,2,4,4,6-pentamethylheptane), isodecane, and isohexadecane.

In some particular embodiments the composition may comprise isohexadecane.

The amount of each of the at least one solvent, when present, is in a range of from about 0.5% to about 15% by weight, or from about 0.5% to about 5% by weight, or from about 1% to about 2% or any suitable combination, sub-combination, range, or sub-range thereof by weight, based on the weight of the composition. One of ordinary skill in the art, however, will appreciate that other ranges are within the scope of the invention.

Thus, each of the at least one solvent in the composition may be present by weight, based on the total weight of the composition, from about 0.5, 1, 2, 3, 4, 5, 6, 7, 8, 9, 10, 11, 12, 13, 14 to about 15 percent, including increments and ranges therein and there between.

In some embodiments, the composition can include one or more additional solvents, for example, monoalcohols such as monohydric C1-C8 alcohols such as ethanol, propanol, butanol, isopropanol, isobutanol, and benzyl alcohol, and phenylethyl alcohol.

Optional Additives

The compositions can also comprise at least one additive used in the cosmetics field which does not affect the properties of the compositions according to the invention, such as fragrances, preservatives/anti-microbials, actives (for example, vitamins, panthenol, tocopherol), coloring materials; including; essential oils; citric acid, sodium chloride; neutralizing or pH-adjusting agents (e.g., triethylamine (TEA) and sodium hydroxide), and combinations thereof.

Although the optional additives are given as examples, it will be appreciated that other optional components compatible with cosmetic applications known in the art may be used that are suitable for an essentially anhydrous composition.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Article/Substrate

In accordance with the various embodiments, provided are articles comprising a solid substrate imbued with an inventive makeup removal composition. The makeup removal and cleansing article is formed from synthetic materials or formed from natural biodegradable and sustainably sourced natural originated fiber, natural fiber, or regenerated or recycled natural fiber.

According to some embodiments, the substrate is a nonwoven material. A general description of nonwoven materials is given in Riedel "Nonwoven Bonding Methods and Materials", Nonwoven World (1987). These substrates are obtained according to the normal methods of the technology for the preparation of nonwoven materials.

When the substrate is a nonwoven material, use may be made of a nonwoven material which does not go into ball and which is sturdy enough not to disintegrate and not to become fluffy when applied to the skin. It must be absorbent and soft at least on one side for the removal of makeup from the eyes in particular. Mention may be made, as appropriate nonwoven materials, for example, of those sold under the names Ultraloft 15285-01, Ultraloft 182-008, Ultraloft 182-010 and Ultraloft 182-016 by BBA, Vilmed M1519 Blau, Vilmed M 1550 N and 112-132-3 by Freudenberg, that sold under the name Norafin 11601-010B by Jacob Holm Industries, the flocked nonwoven materials sold under the names Univel 109 and Univel 119 by Uni Flockage and that made of viscose/PLA supplied by Sandler.

According to some embodiments comprising an article, a water insoluble substrate is employed. The water-insoluble substrate can comprise one or more layers and it can be chosen from the group consisting of woven materials, nonwoven materials, foams, sponges, waddings, as sheets, balls or films. It can in particular be a nonwoven substrate based on fibers of natural origin (flax, wool, cotton, silk, viscose, fibers made of bamboo) or synthetic origin (cellulose derivatives, polyvinyl derivatives, polyesters, such as poly(ethylene terephthalate), polyolefins, such as polyethylene (PET) or polypropylene, polyamides, such as Nylon, or acrylic derivatives) and their mixtures, such as viscose/PET, polylactic acid (PLA) or viscose/polylactic acid (viscose/PLA).

According to one embodiment, the substrate is a nonwoven material, composed of viscose or a nonwoven material composed of a viscose/microviscose mixture, through a hydro entanglement process.

In some particular embodiments, the makeup removal and cleansing article comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these.

According to one embodiment, the substrate is a nonwoven material formed of a biodegradable material, such as lyocell.

According to some embodiments, the substrate can comprise one or more layers having identical or different properties and having properties of elasticity and of softness and other properties appropriate to the desired use. The substrates can comprise, for example, two parts having different elasticity properties, as described in the document WO-A-99/13861, or can comprise a single layer having different densities, as described in the document WO-A-99/25318, or can comprise two layers of different textures, as described in the document WO-A-98/18441.

According to some embodiments, when the article is used for the body, the substrate can comprise at least one rough side for making it possible, at the same time, to massage the skin or to scrub the skin.

According to the various embodiments, the substrate can have any size and any shape which are appropriate for the desired objective. Furthermore, it generally has a surface area of between 0.005 m$^2$ and 0.1 m$^2$, or from between 0.01 m$^2$ and 0.05 m$^2$. The weight of the substrate can be in a range between 30 gsm to 200 gsm (gram per square meter), or from between 40 gsm to 60 gsm.

In accordance with some embodiments, an article according to the disclosure includes one or more sheets or layers of water-soluble substrates infused with the makeup removing composition hereof. Such water-soluble sheet containing articles can provide the user with a complete product for facial cleansing routine that includes all necessary components such as makeup remover and cleanser and does not require the use of additional liquid components. For example, in one embodiment, the wipe comprises at least one sheet that can be used as a makeup removal sheet, e.g., a non-woven sheet comprising fibers that have a texture. This sheet can also incorporate a makeup removal composition according to the instant disclosure, and in some embodiments may include additional layers or portions that include a surfactant component or other oil cleanser as described below. After using such a wipe to remove makeup and/or oils and dirt from the surface of the skin (e.g., face), the wipe can be quickly dissolved in the palm of the consumer's hand, and can be either rinsed away with no or negligible solid waste, or can be used to reconstitute a liquid surfactant product that can be used for further cleansing. In some embodiments, the wipe may comprise two or more layers or sheets that have distinct functions and/or are distinctly functionalized. For example, in one embodiment, the wipe comprises one or more makeup removal sheets that include a makeup removal composition according to the instant disclosure, and in one example, a cleansing sheet comprising a surfactant composition, for example, dry surfactant composition, associated with the sheet. In certain embodiments, the wipe may further comprise one or more exfoliating sheets. And in some examples, an article comprising a wipe may include one or more sheets that are not water soluble.

Figure 2:
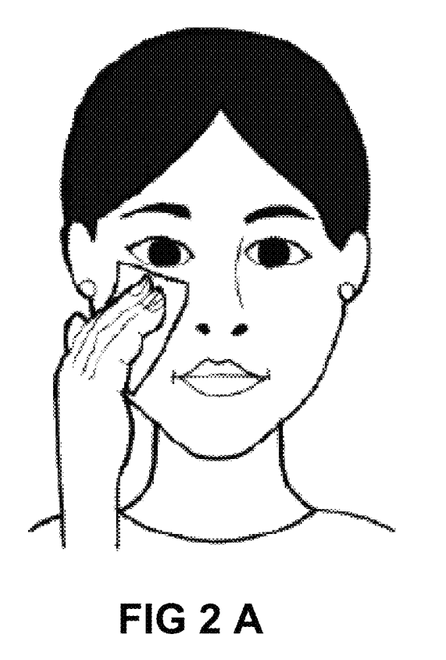
FIG. 2A demonstrates a first step in a representative facial cleansing routine using an embodiment of an inventive article according to the disclosure, specifically using the article to remove makeup, e.g., with oil-based/anhydrous inventive juice composition.
FIG. 2B demonstrates a second step in a representative facial cleansing routine using an embodiment of an inventive article according to the disclosure, specifically wet cleansing sheet with water, by rinsing it lightly under water.
FIG. 2C demonstrates a third step in a representative facial cleansing routine using an embodiment of an inventive article according to the disclosure, specifically using water-rinsed sheet on face.
FIG. 2D demonstrates a fourth step in a representative facial cleansing routine using an embodiment of an inventive article according to the disclosure, specifically depicting how the article dissolves into a foam that the user can rinse off or use for further cleansing.
Figure 3A:
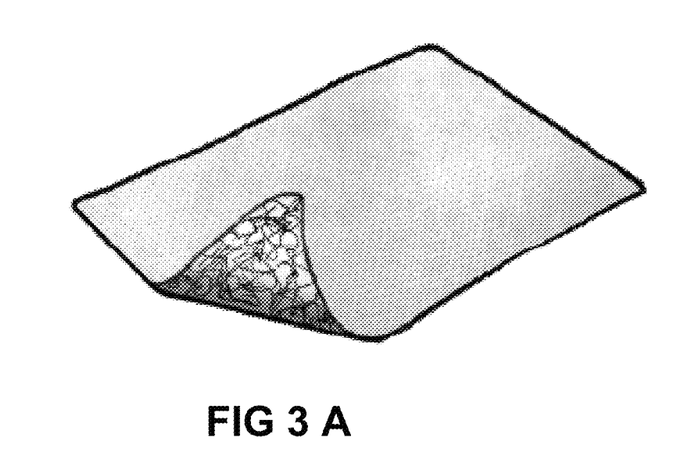
FIG. 3A shows an exemplary article in the form of a regular nonwoven single layer wipe.
Figure 3B:
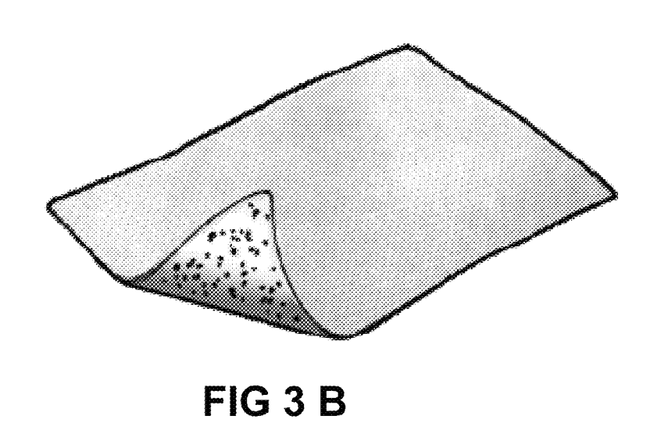
FIG. 3B shows an exemplary article in the form of a regular nonwoven single sheet wipe with heat-sealed edges (FIG. 2B)
Figure 3C:
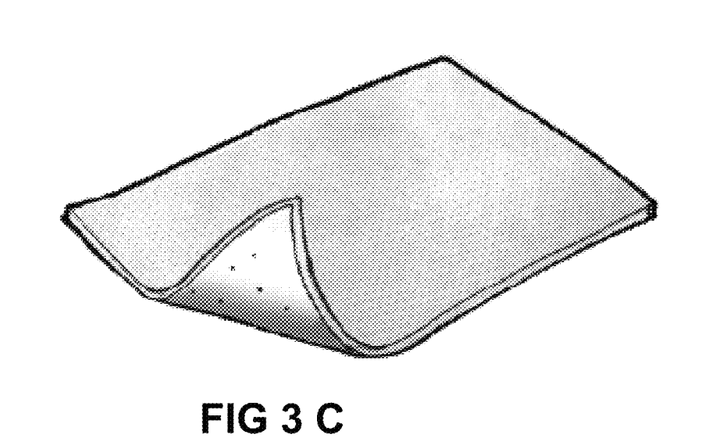
FIG. 3C shows an exemplary article in the form of a regular nonwoven layered pad wipe heat-sealed edges (FIG. 2C)
Figure 3D:
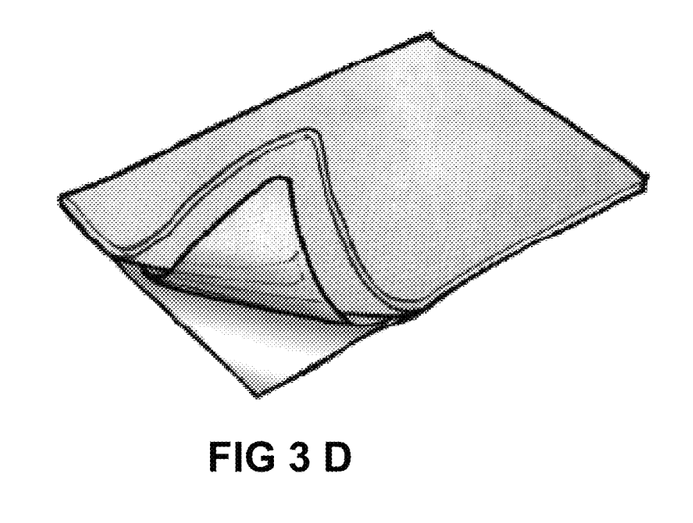
FIG. 3D shows an exemplary article in the form of a regular nonwoven layered wipe with an oil-soaked polyvinyl alcohol (PVA) fiber layer (makeup removing) sheet on one side, PVA cleansing sheet on the other side, and an embedded PVA film on the inside.
Figure 4:
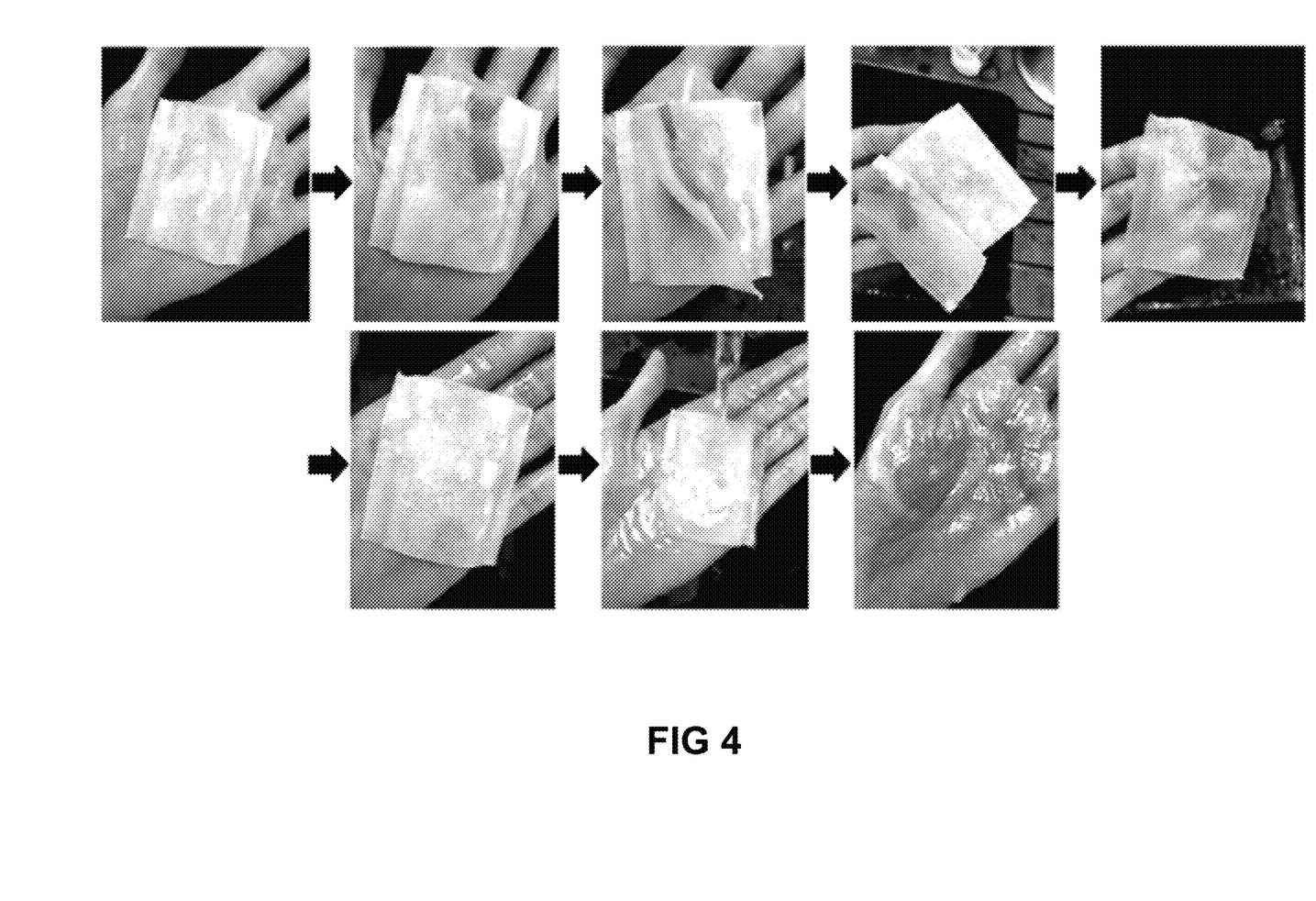
FIG. 4 shows a series of photographs of makeup removal and cleansing using an exemplary wipe.

Articles that comprise more than one sheet and that include water-soluble substrates can be arranged in any manner. In some examples, one or more makeup removing sheets are positioned on the top of one or more cleansing and/or exfoliating sheets. The user can detach a makeup removing sheet from the wipe and use the sheet to wipe the skin to remove makeup and/or dirt. The used sheet can then be discarded by flushing or dissolving under running water. Following the makeup removal, the user can reconstitute the remaining sheet or sheets in water to provide a surfactant cleanser and use the cleanser to wash the skin. FIG. 2 and FIG. 4 show alternate depictions of the use of sheets that include water soluble substrates. With reference now to FIG. 3, articles comprising a wipe can comprise two or more sheets sealed together at the edges and a cleansing pod between two adjacent sheets, wherein the cleansing pod comprises a cleansing composition encapsulated in a water-soluble non-woven wipe or water-soluble film. In some embodiments, when a wipe comprises two or more sheets, the two or more sheets may be detachable. It will be appreciated that while description herein may pertain to sheets that are formed of one or the other of soluble and insoluble substrates, one of ordinary skill will appreciate that the images shown in FIG. 3 with respect to some examples of layered wipes, such examples may include one or both of soluble and insoluble layers.

Generally, with respect to articles that comprise a wipe as disclosed herein, the wipe can have any shape, e.g., a shape appropriate to the intended use, such as for removal of makeup around the eye. For example, the wipe can have a rectangular, round, kidney, or oval shape that has dimensions suitable for the intended use. Thus, the wipe can be of oval shape about 2 cm to 15 cm long and about 1 cm to 10 cm wide, or of disc shape with a diameter of about 2 cm to 15 cm, or in the form of a square with sides of about 5 cm to 15 cm, or in the form of a rectangle about 5 cm to 15 cm long.

In accordance with embodiments of wipes that comprise water-soluble substrate, the substrate is completely or at least substantially soluble in tap water of a temperature suitable for facial cleansing, for example, a temperature of 30° C. or lower. As used herein, "30° C. or lower" means a temperature that does not exceed 30° C. but is not less than 0° C., such as a temperature of from about 0° C. to about 30°

C., or for example, ranging from more than about 0° C. to about 30° C., from about 5° C. to about 30° C., from about 10° C. to about 30° C., from about 15° C. to about 30° C., or from about 20° C. to about 30° C. In certain embodiments, the entire wipe is soluble in water at a temperature of 30° C. or lower. According to such embodiments of wipes that comprise water-soluble substrate comprise sheets that are substantially free of water-insoluble fibers. In some embodiments, the wipe includes sheets that consist of fibers that are water-soluble, such as the wipe itself is entirely water-soluble. According to one embodiment of the invention, the sheets do not have any water-insoluble fibers, i.e, the sheets are composed solely of water-soluble fibers, so that the entire sheet is completely soluble in water.

Any suitable water-soluble fibers can be used in the manufacturing of the wipes disclosed herein, such as natural, artificial, or synthetic water-soluble polymeric fibers. In some embodiments, the water-soluble fibers comprise water-soluble polymeric material. Any water-soluble material that can be spun into fibres can be used in the preparation of the sheets of the wipes disclosed herein, such as materials selected from polyvinyl alcohols, hydroxy(C1-C6)alkyl celluloses, methylcelluloses, carboxymethylcelluloses, polyvinylpyrrolidones, polyalkylene oxides, gelatins, copolymers of acrylic acid and methacrylic acid, and combinations thereof.

In certain embodiments, the water-soluble fibers are polyvinyl alcohol (PVA) fibers that are made with polyvinyl alcohol (PVA) by a method that provides the required water solubility of the fiber. The PVA used in the fibers can have various degrees of polymerization. For instance, PVA fibers that are soluble in water at a temperature less than or equal to 30° C. include PVA fibers that are marketed by the Japanese company Kuaray under the trade name Kuralon K-II WN2. The fibers comprises are prepared by a method that includes preparation of a spinning solution by dissolving a water-soluble PVA-based polymer in a first organic solvent, spinning of the solution in a second organic solvent to obtain solidified threads, and wet drawing of the threads from which the first solvent is removed and which are then dried and undergo a heat treatment. These fibers can have a circular cross-section and have a tensile strength of at least 2.7 g/dtex (3 g/d), as described, for example, U.S. Pat. No. 6,106,945A, to Kuraray Co Ltd, the disclosure of which is incorporated herein by reference in its entirety. Other types of fibers in addition or in the place of PVA can be used in the sheets of the wipes disclosed herein, such as but not limited to polysaccharide fibers marketed under the name Lysornb™ by Lysac Technologies, or polyholoside polymer-based fibers such as glucomannan or starch. When a combination of fibers is used in the wipes disclosed herein, where appropriate, the fibers can comprise a mixture of various fibers that are water-soluble at different temperatures, such as different temperatures of 30° C. or lower. In some embodiments, each sheet of the one or more sheets comprises two or more types of water-soluble fibers. In other embodiments, the wipes can comprise two or more sheets wherein at least two sheets comprise a different type of water-soluble material.

In accordance with embodiments wherein an article according to the disclosure includes one or more sheets or layers of water-soluble substrates, such wipes will comprise at least one non-woven sheet. In some embodiments, the non-woven sheet is a spun-wound sheet or a needle-punched sheet. Any suitable techniques for making a nonwoven material from fibers can be used in the manufacturing of the wipes disclosed herein. For example, the fibers can be formed by extrusion and deposited on a conveyor to form a sheet of fibers which is then consolidated by a conventional fiber bonding technique, for example needling, hot bonding, calendaring. In some embodiments, bonding by jets of hot air (i.e., air through bonding), a technique in which the sheet passes through a tunnel into which hot air is blown, can be employed, for example when the sheet is composed of fibers comprising two types of material. Such fibers include fibers comprising at least two grades of polyvinyl alcohol (PVA) of different melting points or softening points. These fibers can be co-extruded in such a way that the fiber has PVA of at least one first grade located in the core of the fiber and PVA of at least one second grade located at the periphery of the fiber, e.g., forming a sheath around the core. Bonding of such core-sheath fibers can be easier achieved when the sheath has a lower melting point than the core. When the wipes disclosed herein comprise several sheets, two or more sheets can be joined together in a variety of ways, for example by welding, gluing, or stitching, for instance, by stitching with a thread that is itself water-soluble. In some embodiments, when the wipe comprises several non-woven sheets, these sheets can be joined together by heat sealing, for example, by heat sealing the edges of the wipes or on their periphery so as to provide a wipe with an internal cavity.

In certain embodiments, the surface of the water-soluble fibers is functionally modified or functionalized by a suitable treatment such as mechanical treatment, chemical treatment, coating, or a combination thereof. Functionalization done through mechanical and/or coating and/or chemical means is used to provide a specific property, such as but not limited to cleansing, absorption, skin exfoliation, containment of active ingredients, deposition of active ingredients, durability, or a combination thereof. In certain embodiments, the fibers are mechanically treated or modified. Mechanical treatment, such as treatment selected from micro-creeping (calendar pressure and heat), mechanical bonding, and a combination thereof, can be used to increase sheet volume, create physical texture, or alter absorption characteristics (e.g., provide more volume or higher absorption rate). In certain embodiments, mechanical bonding, such as heat forming and/or sealing, can create physical textures and alter absorption and dissolution characteristics (i.e., bonds increase dissolution time, reduce absorption rates, and create rough/durable areas), or can be used to create pointed, linear, linear patterns, or co-planar seals. In certain embodiments, the fibers comprise a coating. In some embodiments, the coating is a hydrophobic coating. Coating the fibers of the wipes disclosed herein can be achieved in any suitable manner by contacting the water-soluble fibers with a hydrophobic composition, e.g., a coating can be calendared, sprayed on, fused to, or soaked/saturated within/on the non-woven sheets such as PVA non-woven sheets. Hydrophobic coatings can inhibit solubility with water or provide a barrier on one or both sides of the non-woven sheet. Additionally, film coating can function as a barrier to or between one or more non-woven sheets (eg., PVA sheets) impregnated with incompatible formulas that need to deliver a distinct benefit or effect, e.g. separating PVA sheet soaked in oil for makeup removal from a PVA sheet impregnated with a powder surfactant composition for cleansing and "sudsing" effect, which serves a major efficacy cue for the users, upon contact with water. For example, an exemplary wipe can comprise one or more makeup removal sheets having fibers coated with makeup removal formulation such as an oil. Examples of makeup removing formulations are known in the art.

In certain embodiments of wipes that comprise water-soluble substrate, the fibers comprising the sheets comprise a hydrophobic coating. Suitable hydrophobic coatings include coatings comprising silicone, hydrocarbons, natural oils, glycerin, lycopodium powder, water displacement solvents, or combinations thereof. The coating can further serve as an adhesive for additional functionality, such as powdered detergent or surfactant composition or an exfoliating composition. Surfactants and exfoliating agents are known in the art.

In some embodiments, the wipes disclosed herein comprise a makeup removing sheet which is a textured PVA sheet or a PVA sheet that has a makeup removing agent such as a makeup removal composition according to the instant disclosure, or an additional cleansing oil associated with it. In other embodiments, the wipes further comprise an anhydrous surfactant composition associated with the fibers, as described above. Suitable surfactant compositions can comprise SLS, fats, alkalis, essential oils, fragrances, glycerin, blends, cocoa butter. The surfactants can be dry (powder) or other anhydrous forms (e.g., having less than about 5%, less than about 3%, or less than about 1% by weight water). Yet in further embodiments, in addition to the sheets described herein, the wipe further comprises at least one exfoliating sheet, e.g., a sheet having an exfoliating agent associated with the sheet. Thus, in some embodiments, the wipe comprises multiple sheets, e.g., two or more sheets, three or more sheets, or four or more sheets. In some embodiments, when the wipe comprises two or more sheets, the at least two of the two or more sheets are heat sealed. The wipe disclosed herein can further comprise a barrier film between two adjacent sheets, for example, sheets that have incompatible functionalities or formulae. The film is composed of a water soluble material, for example, in some embodiments, the film comprises polyvinyl alcohol. PVA films are known in the art and are offered commercially by a number of manufacturers. Any thickness sheets can be used in the wipes disclosed herein. In certain embodiments, the sheets have a thickness of from about 0.3 mm to about 0.5 mm. In some embodiments, the sheets have a thickness of about 0.40 mm to about 0.45 mm.

The wipes disclosed herein can be manufactured by methods known in the art, for example, processes disclosed in U.S. Pat. Nos. 7,465,266 and 6,202,845 which are incorporated herein in their entirety. For example, a multi-layered, non-woven exemplary PVA wipe can be manufactured by fusing a non-woven PVA sheet with PVA film to create a multi-layered wipe that separates incompatible formulae. As illustrated in FIG. 3D, three webs, e.g., a makeup removing non-woven PVA fiber sheet, a PVA film, and a cleansing PVA sheet having the characteristics described above, are bought together, in an in-line manufacturing process, using a sealing (layer to layer) step and cutting/scoring step (to allow for "z-folding"), and alternate "z-folding" that allows for compatible formulas on alternating sides of the wipe to be in contact, avoiding two incompatible formulas from touching each other. The method is useful to separate substrates that are impregnated and/or coated with formulae to avoid reaction (e.g., oil/surfactant foam neutralization) during manufacturing and packaging of multi-layer non-woven wipes, and throughout consumer use (i.e., the wipes dispense in a reverse "z-fold").

Generally, articles hereof, including those comprising one or more of insoluble and water-soluble substrates, can be provided in a kit or a package comprising at least one wipe as disclosed herein. In some embodiments, the kit comprises multiple wipes. In certain embodiments, the wipes are removably attached to each other and/or folded into a reverse z-fold as described above.

According to the various embodiments, the degree of impregnation of the composition onto the substrate generally ranges from 100 to 1000%, in some embodiments from about 150% to about 700%, or from about 250% to about 400% of the weight of the substrate. The techniques for impregnating the substrates with compositions are well known and can all be applied in the present invention. Generally, the impregnating composition is heated and added to the substrate by one or more techniques comprising immersion, coating, spraying, and the like.

The examples below according to the invention are given by way of illustration and without a limiting nature. The names are the chemical name or the INCI name. The amounts are given therein as % by weight, unless otherwise mentioned.

EXAMPLES

Example 1: Raw Materials

TABLE 1

Raw Materials

| Phase | INCI Name | Notes and Commercial Sources |
|---|---|---|
| A | ZEA MAYS (CORN) GERM OIL | |
| A | ISOPROPYL PALMITATE | |
| A | ISOPROPYL MYRISTATE | |
| A | DICAPRYLYL ETHER | |
| A | ISOHEXADECANE | |
| A | TOCOPHEROL | |
| A | PHENOXYETHANOL | |
| A | Fragrance | |
| B | ETHYLHEXYL PALMITATE | |
| B | POLYGLYCERYL-6 DICAPRATE | TAIYO KAGAKU - SUNSOFT Q-102H-C |
| B | POLYGLYCERYL-2 OLEATE | TAIYO KAGAKU - SUNSOFT Q-17D(G)-C |
| B | POLYGLYCERYL-10 DIOLEATE (and) TOCOPHEROL | TAIYO KAGAKU - SUNSOFT Q-172Y-C |

Example 2: Inventive Compositions

Various representative embodiments of the inventive compositions and articles are exemplified herein. In some instances, the composition is referred to as a "juice." Inventive compositions in juice form (not imbued in a substrate) are designated with a numeric identifier (e.g., "Inventive Composition 1" or "INV 1"); inventive compositions in article form (imbued in a substrate) are designated with an alphanumeric identifier (e.g., "Inventive Composition 1A" or "INV 1A" (juice imbued in a water-soluble PVOH nonwoven); "Inventive Composition 1B" or "INV 1B" (juice imbued in a synthetic nonwoven substrate)).

TABLE 2

Inventive Compositions

| | InventiveExamples | Inventive Ex. 1 | Inventive Ex. 2 |
|---|---|---|---|
| Phase | INCI Name | Wt % | Wt % |
| A | ZEA MAYS (CORN) GERM OIL | 37.35 | 21.35 |
| A | ISOPROPYL PALMITATE | 20 | 20 |

TABLE 2-continued

Inventive Compositions

| Phase | INCI Name | Inventive Ex. 1 Wt % | Inventive Ex. 2 Wt % |
|---|---|---|---|
| A | ISOPROPYL MYRISTATE | 18 | 20 |
| A | DICAPRYLYL ETHER | 2 | 5 |
| A | ISOHEXADECANE | | 5 |
| A | TOCOPHEROL | 0.1 | 0.1 |
| A | PHENOXYETHANOL | 0.5 | 0.5 |
| A | Fragrance | 0.05 | 0.05 |
| B | ETHYLHEXYL PALMITATE | 20 | 25 |
| B | POLYGLYCERYL-6 DICAPRATE | 1 | 1 |
| B | POLYGLYCERYL-2 OLEATE | 1 | 1 |
| B | POLYGLYCERYL-10 DIOLEATE (and) TOCOPHEROL | | 1 |
| | Total (%): | 100 | 100 |

Example 3: Inventive Composition Preparation Procedures

Preparation of juice formulas: 1. Add Phase A into main kettle (MK) and mix well at room temp, giving a clear, light yellow liquid. 2. In a side kettle (SK) premix Phase B and heat to 70-75° C. Mix well and make sure Phase B is fully soluble, giving a colorless clear liquid. 3. When Phase B is fully dispersed add Phase B into MK slowly. Keep mixing MK as Phase B is added slowly, ensuring the mixture is fully homogenous. 4. As Phase B is added into MK the batch will become more translucent and clear. The formula has a translucent, light yellow color. 5. Cool to room temp and drop the batch.

The inventive compositions are essentially anhydrous, clear liquids with some or no light yellow coloration.

Preparation of makeup removing wipes: Homogeneously soak the chosen nonwoven substrate with a juice formulation in a weight percent ratio of 1:2.5 (substrate: juice formula) manner. Fold the wet substrates into a desired shape, stack the folded wet wipes and pack into a suitable package for ease of use.

Example 4: Inventive Wipes

TABLE 3

Inventive Wipe Compositions

| Inventive Wipes | Juice Composition | Substrate Composition | Juice: Substrate (wt) |
|---|---|---|---|
| Ex 1A | INV Ex.1 | 100% PVOH (water-soluble) | 2.5:1 |
| Ex 1B | INV Ex.1 | 50% PET, 32% Viscose, 18% PP | 2.5:1 |
| Ex 2A | INV Ex.2 | 100% PVOH (water-soluble) | 2.5:1 |

Example 5: Comparative Compositions

TABLE 4

Comparative Composition 1 - NEUTROGENA (™) Makeup Remover Cleansing Towelettes (weight composition is based on Example 18 from U.S. Pat. No. 7,262,158 and chromatographic analysis results)

| Ingredients | Weight (g) |
|---|---|
| Water (QS) | 866.663 |
| Cetyl Ethylhexanoate | 20 |
| Isostearyl Palmitate | 20 |
| Pentaerythrityl Tetraethylhexanoate | 20 |
| Isononyl Isononanoate | 20 |
| Cyclopentasiloxane | 20 |
| Hexylene Glycol | 10 |
| PEG-6 Caprylic/Capric Glycerides | 7.5 |
| PEG-4 Laurate (and) Sucrose Cocoate | 10 |
| Carbomer | 5 |
| Sodium Hydroxide | QS to pH 5.5 |
| Benzoic Acid | 0.47 |
| Dehydroacetic Acid | 0.069 |
| Phenoxyethanol | 6.5 |
| Iodopropynyl Butylcarbamate | 0.29 |
| Fragrance (EU 1279) | 0.5 |
| Total Wt (g) | 1000 |

TABLE 5

Comparative Composition 2 - GARNIER (™) Clean + Refreshing Towelettes

| Ingredients | Weight Percent* |
|---|---|
| Aqua/Water | |
| Isohexadecane* | 1.99 |
| Dicaprylyl Ether* | 1.98 |
| Vitis Vinifera Fruit Water/Grape Fruit Water | |
| Hexylene Glycol | |
| Phenoxyethanol | |
| Sorbitan Laurate | |
| Acrylates/C10-30 Alkyl Acrylate Crosspolymer | |
| Tetrasodium Glutamate Diacetate | |
| Propylene Glycol | |
| Aminomethyl Propanol | |
| Parfum/Fragrance | |
| Lauryl Glucoside | |
| Polyglyceryl-2 Dipolyhydroxystearate | |
| Glycerin | |
| Citric Acid | |
| Iodopropynyl Butylcarbamate | |
| Linalool | |
| Benzyl Salicylate | |
| Limonene | |
| Pentylene Glycol | |
| Mentha Piperita Extract/Peppermint Extract | |
| Benzyl Alcohol | |
| Tocopherol | |
| Tocopheryl Acetate | |

*Weight percentage is based on chromatographic analysis results.

TABLE 6

Comparative Composition 3 - Shiseido - Clé de Peau Beauté Eye and Lip Makeup Remover Towelettes (oil-based make up removing wipes)

Ingredients

CYCLOMETHICONE
MINERAL OIL (PARAFFINUM LIQUIDUM/HUILE MINERALE)
C13-14 ISOPARAFFIN

TABLE 6-continued

Comparative Composition 3 - Shiseido - Clé de Peau Beauté Eye and Lip Makeup Remover Towelettes (oil-based make up removing wipes)

Ingredients

DIMETHICONE
ARGANIA SPINOSA KERNEL OIL
PHYTOSTERYL/OCTYLDODECYL LAUROYL GLUTAMATE
TOCOPHEROL
MORTIERELLA OIL(HUILE DE MORTIERELLA)
FRAGRANCE (PARFUM)
CAMELLIA JAPONICA SEED OIL
LIMONENE

Example 6: Expert Evaluation

Demonstration of the effectiveness of inventive compositions vs comparative compositions in stubborn makeup and mascara removal.

Figure 1:
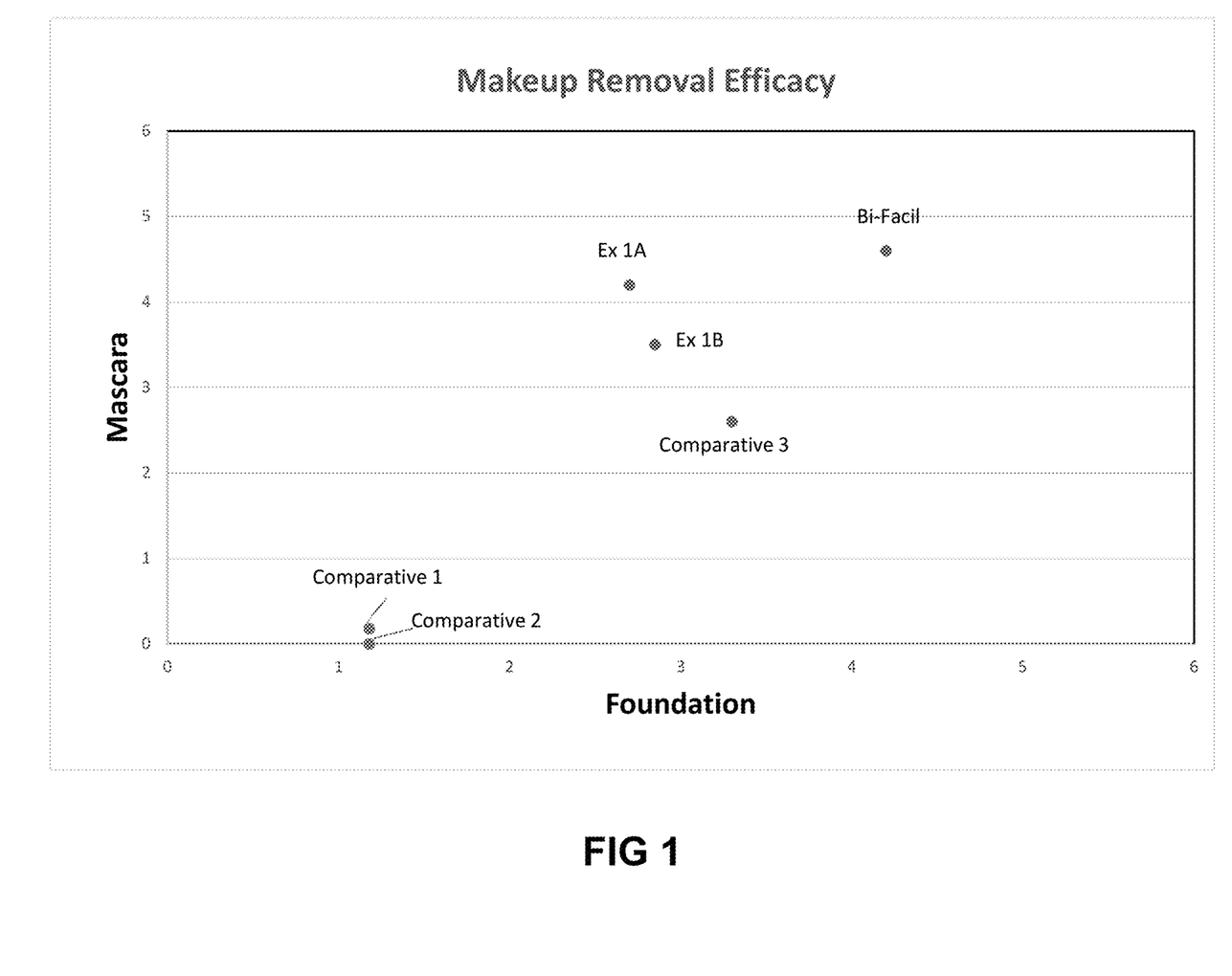
FIG. 1 is a data plot in the form of a 2D graph that shows the makeup removal efficacy of inventive compositions according to the disclosure and comparative compositions.

A study was conducted to evaluate the effectiveness of the inventive compositions in comparison with commercially available makeup removing wet wipes (comparative compositions), having generally similar components infused in a solid substrate. In the study, wipe substrates impregnated with juice compositions were used by trained/expert aesthetician to remove heavy face makeup (Maybelline™ Super Stay Full Coverage Foundation), and mascara (Maybelline™ Colossal Big Shot Waterproof Mascara). The cleansing wipes were prepared by soaking the liquid cleaning composition with a wipe substrate in a specific weight percentage ratio, typically 2.5:1 (juice: substrate). The makeup removal efficacy was determined by following a protocol under which the aesthetician applied stubborn makeup products on six (6) Caucasian women. After 30 min, the aesthetician removed the makeup with test products (inventive and comparative) and the degree of removal was assessed by the amount of residual makeup that was removed by using Lancome™ Bi-Facil™ Makeup Remover (a two-phase make-up removal product), 2 mL on a cotton pad for up to 6 cotton pads. The higher the makeup removal efficacy of the test formula would require fewer cotton pads with Bi-Facil™ to remove, as there would be less residual makeup. The makeup removal efficacy data was plotted using a 2D graph, shown as FIG. 1; the data as shown in FIG. 1 are represented in Table 7.

TABLE 7

Make-Up Removal Efficacy (scale of 1 to 6: 6 being complete removal, and 1 being no removal)

| Test Composition | Foundation | Mascara |
| --- | --- | --- |
| Neutrogena (™) (Comparative 1) | 1.18 | 0.18 |
| Garnier Wipes (™) (Comparative 2) | 1.18 | 0 |
| Cle de Peau (Comparative 3) | 3.3 | 2.6 |
| Bi-Facil (Two-phase product) | 4.2 | 4.6 |
| Inventive Ex 1A | 2.85 | 3.5 |
| Inventive Ex 1B | 2.7 | 4.2 |

Both tested inventive compositions are more efficient in foundation and mascara removal as compared with each of the comparative compositions, and both inventive compositions provided aesthetically acceptable results.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A makeup removal composition, comprising:
   i. at least one branched, alkylated alcohol ester present from about 40% to about 70% by weight of the composition;
   ii. at least one dialkylated ether, dialkylated carbonate, or a combination thereof present from about 2% to about 20% by weight of the composition;
   iii. at least one nonionic surfactant present from about 0.5% to about 5% by weight of the composition; and
   iv. at least one vegetable derived oil present from about 20% to about 60% by weight of the composition, wherein the composition is essentially free of water and silicone.

2. The makeup removal composition according to claim 1, wherein:
   i. the at least one branched, alkylated alcohol ester comprises one or more of isopropyl myristate, isopropyl palmitate, ethylhexyl palmitate;
   ii. the at least one dialkylated ether, dialkylated carbonate, or a combination thereof comprises one or more of dicaprylyl ether and dicaprylyl carbonate;
   iii. the at least one nonionic surfactant comprises one or more of polyglyceryl-6 dicaprate, polyglyceryl-2 oleate and polyglyceryl-10 dioleate; and
   iv. the at least one vegetable derived oil comprises one or more of zea mays (corn) oil or brassica campestris (rapeseed) seed oil.

3. The makeup removal composition according to claim 1, comprising a solvent that comprises isohexadecane.

4. The makeup removal composition according to claim 1, wherein the at least one polar emollient with molecular weight of 400 g/mol or less is present from about 5% to about 10% by weight of the composition.

5. The makeup removal composition according to claim 1, wherein the composition is essentially free of mineral oil.

6. The makeup removal composition according to claim 1, wherein:
   i. the at least one branched, alkylated alcohol ester comprises isopropyl myristate, isopropyl palmitate, and ethylhexyl palmitate, each of the isopropyl myristate, isopropyl palmitate, and ethylhexyl palmitate present from about 20% to about 25% by weight of the composition;
   ii. the at least one dialkylated ether, dialkylated carbonate or combination thereof comprises dicaprylyl ether, the dicaprylyl ether present from about 3% to about 5% by weight of the composition;
   iii. the at least one nonionic surfactant comprises polyglyceryl-6 dicaprate and polyglyceryl-2 oleate, each of the polyglyceryl-6 dicaprate and polyglyceryl-2 oleate present from about 1% to about 3% by weight of the composition; and
   iv. the at least one vegetable derived oil comprises zea mays (corn) oil from about 10% to about 30%.

7. A makeup removal and cleansing article, comprising:
   a. A substrate;
   b. Impregnated in the substrate a cleansing composition comprising:
   i. at least one branched, alkylated alcohol ester present from about 40% to about 70% by weight of the composition;
   ii. at least one dialkylated ether, dialkylated carbonate or a combination thereof, present from about 2% to about 20% by weight of the composition;
   iii. at least one nonionic surfactant present from about 0.5% to about 5% by weight of the composition; and
   iv. at least one vegetable derived oil present from about 20% to about 60% by weight of the composition, wherein the composition is essentially free of water and silicones, and
   wherein the cleansing composition is impregnated onto the substrate in a soaking rate of 250% to 400% by weight of the cleansing composition to the weight of the substrate.

8. The makeup removal and cleansing article according to claim 7, wherein the substrate is water insoluble.

9. The makeup removal and cleansing article according to claim 7, wherein the substrate is water soluble.

10. The makeup removal and cleansing article according to claim 7, wherein:
   i. the at least one branched, alkylated alcohol ester comprises isopropyl myristate, isopropyl palmitate, and ethylhexyl palmitate, each of the isopropyl myristate, isopropyl palmitate, and ethylhexyl palmitate present from about 20% to about 25% by weight of the composition;
   ii. the at least one dialkylated ether, dialkylated carbonate or combination thereof comprises dicaprylyl ether, the dicaprylyl ether present from about 3% to about 5% by weight of the composition;

iii. the at least one nonionic surfactant comprises polyglyceryl-6 dicaprate and polyglyceryl-2 oleate, each of the polyglyceryl-6 dicaprate and polyglyceryl-2 oleate present from about 1% to about 3% by weight of the composition; and iv. the at least one vegetable derived oil comprises zea mays (corn) oil from about 10% to about 30%.

11. The makeup removal and cleansing article according to claim 8, wherein the article is a cosmetic removal wipe that comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these.

12. The makeup removal and cleansing article according to claim 8, wherein the composition is essentially free of mineral oil.

13. A makeup removal and cleansing article, comprising:
a. A water-soluble substrate comprising a cosmetic wipe;
b. Impregnated in the water-soluble substrate a cleansing composition comprising:
  i. at least one branched, alkylated alcohol ester present from about 40% to about 70% by weight of the composition;
  ii. at least one dialkylated ether, dialkylated carbonate or a combination thereof, present from about 2% to about 20% by weight of the composition;
  iii. at least one nonionic surfactant present from about 0.5% to about 5% by weight of the composition; and
  iv. at least one vegetable derived oil present from about 20% to about 60% by weight of the composition,
    wherein the composition is essentially free of water and silicones, and
    wherein the cleansing composition is impregnated onto the substrate in a soaking rate of 250% to 400% by weight of the cleansing composition to the weight of the substrate.

14. The makeup removal and cleansing article according to claim 13, wherein the composition is essentially free of mineral oil.

15. The makeup removal and cleansing article according to claim 13, wherein the makeup removal and cleansing article comprises one or more nonwoven sheets comprising water-soluble fibers, wherein the sheets are soluble in running or standing water having a temperature of 30° C. or less and durable when contacted with an anhydrous formulation comprising 5% based on the weight of the composition of water or less.

16. The makeup removal and cleansing article according to claim 13, wherein the makeup removal and cleansing article comprises water-soluble fibers that comprise polyvinyl alcohols, hydroxy(C1-C6)alkyl celluloses, methylcelluloses, carboxymethylcelluloses, polyvinylpyrrolidones, polyalkylene oxides, gelatins, copolymers of acrylic acid and methacrylic acid, or combinations thereof.

17. The makeup removal and cleansing article according to claim 13, wherein at least one sheet of the one or more sheets is spun-wound non-woven sheet or needle-punched non-woven sheet.

18. The makeup removal and cleansing article according to claim 13, wherein the water-soluble fibers are characterized as one of comprising polyvinyl alcohol fibers, is functionally modified by mechanical treatment, chemical treatment, or coating, comprises a hydrophobic coating.

19. The makeup removal and cleansing article according to claim 13, wherein the article comprises a cleansing pod between two adjacent sheets, wherein the cleansing pod comprises a cleansing composition encapsulated in a water soluble nonwoven wipe or water soluble film.

20. The makeup removal and cleansing article according to claim 13, wherein:
i. the at least one branched, alkylated alcohol ester comprises isopropyl myristate, isopropyl palmitate, and ethylhexyl palmitate, each of the isopropyl myristate, isopropyl palmitate, and ethylhexyl palmitate present from about 20% to about 25% by weight of the composition;
ii. the at least one dialkylated ether, dialkylated carbonate or combination thereof comprises dicaprylyl ether, the dicaprylyl ether present from about 3% to about 5% by weight of the composition;
iii. the at least one nonionic surfactant comprises polyglyceryl-6 dicaprate and polyglyceryl-2 oleate, each of the polyglyceryl-6 dicaprate and polyglyceryl-2 oleate present from about 1% to about 3% by weight of the composition; and
iv. the at least one vegetable derived oil comprises zea mays (corn) oil from about 10% to about 30%, wherein the cleansing composition is impregnated onto the substrate in a soaking rate of 300% by weight of the cleansing composition to the weight of the substrate.

* * * * *